United States Patent [19]

Matsushita et al.

[11] 4,171,430

[45] Oct. 16, 1979

[54] SEPARATION OF SWEET COMPONENT FROM NATURAL SWEET EXTRACTS

[75] Inventors: Susumu Matsushita; Tetsuo Ikushige, both of Shin-nanyo, Japan

[73] Assignee: Toyo Soda Manufacturing Co., Ltd., Yamaguchi, Japan

[21] Appl. No.: 828,201

[22] Filed: Aug. 26, 1977

[30] Foreign Application Priority Data

Sep. 16, 1976 [JP] Japan .................................. 51-109856

[51] Int. Cl.² ............................................. C07H 1/08
[52] U.S. Cl. .................................... 536/8; 260/236.5; 260/343.5; 536/4
[58] Field of Search ................. 536/4, 8, 1; 260/343.5, 260/236.5

[56] References Cited

U.S. PATENT DOCUMENTS

| | | | |
|---|---|---|---|
| 2,500,930 | 3/1950 | Couch et al. | 536/8 |
| 2,524,414 | 10/1950 | Wolfrom et al. | 536/4 |
| 2,681,907 | 6/1954 | Wender | 536/8 |
| 2,738,346 | 3/1956 | Wender | 536/8 |
| 3,238,190 | 3/1966 | Erbring et al. | 536/4 |
| 3,723,410 | 3/1973 | Persinos | 536/4 |

*Primary Examiner*—Johnnie R. Brown
*Attorney, Agent, or Firm*—Oblon, Fisher, Spivak, McClelland & Maier

[57] ABSTRACT

Glycosides such as stevioside, glycyrrhizin and neohesperidin dihydrochalcone are separated from non-glycosides such as phyllodulcin and perillartine by column chromatography using a porous gel.

7 Claims, 1 Drawing Figure

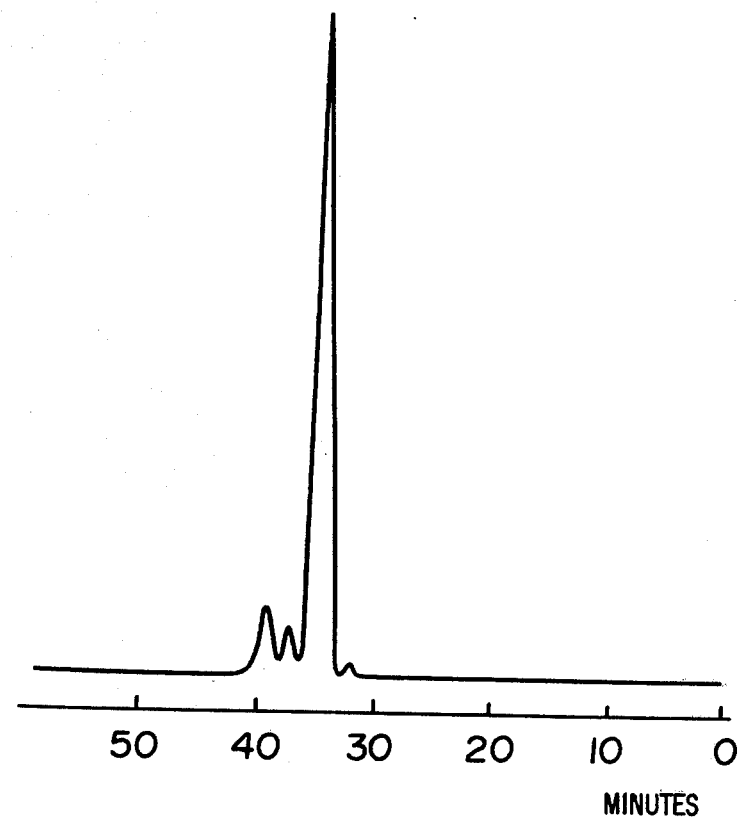

SEPARATION OF SWEET COMPONENT FROM NATURAL SWEET EXTRACTS

BACKGROUND OF THE INVENTION:

1. Field of the Invention

The present invention relates to a method of separating sweet glycosides or non-glycosides from natural sweet extracts.

2. Description of the Prior Art

The natural sweet extracts can be obtained by extractions of leaves, roots or fruits of natural plants in the form of liquid or solid. Some natural sweet extracts have sweetness higher than saccharose. For examples, stevioside extracted from leaves of Stevia; glycyrrhizin extracted from root of Kanzō and phyllodulcin extracted from Amachia have sweetness of more than 300 times of sweetness. These natural sweet compounds are glycosides or non-glycosides having a molecular weight of about 250 to 1000.

It has been known to separate the natural sweet compounds from the extract obtained by extracting leaves, roots or fruits of plants by a gas-chromatography or a thin layer chromatography, etc. However, any satisfactory separating method has not been found.

In the gas-chromatography, it is necessary to convert the natural sweet compounds to the corresponding volatile compound by the trimethylsilylation or the Smith decomposition because the natural sweet compounds are involatile compounds.

On the other hand, in the thin layer chromatography, it is not enough to separate the natural sweet compound and it takes a long time for development separation.

SUMMARY OF THE INVENTION

It is an object of the present invention to provide a method of separating a natural sweet compound from an extract in an industrial scale by a fast and simple operation.

It is another object of the present invention to provide a method of preparing stevioside, glycyrrhizin, neohesperidin dihydrochalcone, phyllodulcin or perillartine from extracts by simple and effective industrial operation.

The foregoing and other objects of the present invention have been attained by separating the natural sweet compound from the extract of a plant by column chromatography using porous gel such as nonpolar crosslinked styrene type gel or polar crosslinked starch type gel which has pore diameters of less than $1 \times 10^4$ Å.

DETAILED DESCRIPTION OF THE PREFERRED EMBODIMENTS:

The extracts obtained by extracting from leaves, roots or fruits of sweet plants contain natural sweet compounds such as stevioside, glycyrrhizin, neohesperidin dihydrochalcone, phyllodulcin and perillartine as well as the other cosolutes such as plastids and inorganic compounds and the solvent for the extraction. The solvents can be ones which dissolve the object sweet compounds and preferably the same with the eluent for the column chromatography.

The filler for the column chromatography used in the present invention is preferably a porous gel which has pore diameters controlled less than $1 \times 10^4$ Å preferably less than $2.5 \times 10^2$ Å. The porous gels can be nonpolar crosslinked styrene type gels and polar crosslinked starch type gels. The gels having pore diameters of more than $1 \times 10^4$ Å are not used in the method of the present invention. The pore diameter of the porous gels means the maximum linear molecular chain length of the molecules which can be immersed into the gel.

When the nonpolar crosslinked styrene type gel is used as the filler for the column chromatography, a non-aqueous solvent is used as the elute and chloroform, methylethyl ketone, ethyl acetate, water, and mixtures thereof cannot be used as the eluent. On the other hand, when polar crosslinked starch gel is used as the filler for the column chromatography, a mixture of organic solvent containing 4 to 40 wt.% of water is used as the eluant. The organic solvents can be $C_1-C_4$ alcohols (methyl alcohol, ethyl alcohol, isopropyl alcohol, n-butyl alcohol), acetonitrile, dioxane, tetrahydrofuran, dimethylformamide or mixture thereof.

In the former case, tetrahydrofuran is preferable and in the latter case, acetonitrile is preferable.

When the water content is more than 40% in the latter case, the separation is not enough. When the water content is less than 4%, the natural sweet compound is adsorbed in the porous gel. Even though the adsorption is not remarkable, the time required for the separation is too long.

The present invention will be illustrated.

EXAMPLE 1

Stevioside, glycyrrhizin acid, phyllodulcin and sodium saccharine (about 1 g of each compound) were measured and dissolved to prepare 1 liter of an aqueous solution.

Chromatography apparatus HLC-802-UR manufactured by Toyo Soda Manufacturing Co., Ltd. was used and tetrahydrofuran as the eluent was used to control the flow rate of 1.0 ml/min.

Styrene type gel having different hole diameter manufactured by Toyo Soda Manufacturing Co., Ltd. shown Table 1 was used as a column packing to study the separatability of the four components.

As it is clear from Table 1, when the pore diameter of the packing is less than $2.5 \times 10^2$ Å, the four components were completely separated in a short time. When it is in a range of $1.5 \times 10^3$ Å to $1 \times 10^4$ Å, the separability was slightly inferior. When it is more than $1 \times 10^4$ Å, the separation of the four components could not be attained.

Table 1

Effect of pore diameter for separatability of stevioside, glycyrrhizin acid, phyllodulcin and sodium saccharide

| Pore diameter (Å) | Eluted volume (ml) | | | | Separatability |
|---|---|---|---|---|---|
| | ST[1] | GL[2] | PH[3] | SA[4] | |
| $4 \times 10^1$ | 37.7 | 42.3 | 46.2 | 48.1 | excellent |
| $2.5 \times 10^2$ | 47.5 | 51.4 | 54.6 | 56.6 | excellent |
| $1.5 \times 10^3$ | 57.9 | 60.1 | 62.4 | 63.7 | fair |
| $1 \times 10^4$ | 63.1 | 65.0 | 66.3 | 66.4 | fair |
| $1 \times 10^5$ | 66.3 | 67.0 | 67.6 | 68.3 | no good |
| $1 \times 10^6$ | 68.9 | 70.0 | 70.1 | 70.1 | no good |
| $1 \times 10^7$ | 70.2 | 70.2 | 70.3 | 70.3 | no good |

[1]stevioside
[2]glycyrrhizin acid
[3]phyllodulcin
[4]sodium saccharine

REFERENCE 1

In accordance with the process of Example 1 except using water or a mixture of water and methyl alcohol, instead of tetrahydrofuran, the separation of the four components were carried out. The adsorption of the components were too high to separate them.

EXAMPLE 2

An aqueous solution of the sample was prepared by dissolving 1 g of the commercially available stevioside was dissolved in 100 ml of water.

Chromatography apparatus HLC-801A manufactured by Toyo Soda Manufacturing Co., Ltd. was used and the crosslinked starch type gel (hole diameter of $2.5 \times 10^2$ Å) manufactured by Toyo Soda Manufacturing Co., Ltd. was used as a column packing and the flow rate was controlled to 1 ml/min. to separate it.

The separabilities were studied by varying the compositions of mixtures of water/acetonitrile and water/methyl alcohol as shown in Table 2.

As it is clear from Table 2, when a mixture containing water in a range of 4 to 40% for mixtures of water/acetonitrile, and water/methylalcohol, the mutual separation of the commercially available stevioside could be attained. However, the separation could not be attained out of the range.

The ratio of water/acetonitrile of 20/80 was especially preferable. The chromatogram was shown in FIG. 1.

Table 2

Effect of eluent and ratio of components of eluent for separatability of commercially available stevioside.

| components ratio[1] | water/acetonitrile | water/methyl alcohol |
|---|---|---|
| 0/100 | no good | no good |
| 4/96 | fair | fair |
| 10/90 | fair | fair |
| 20/80 | excellent | fair |
| 30/70 | fair | fair |
| 40/60 | fair | fair |
| 50/50 | no good | no good |
| 60/40 | no good | no good |

[1]composition of water/organic solvent

EXAMPLE 3

A 100 g of stevia dried leaves was treated in 1 liter of stirred water at 50° C. for 1 hour to extract stevioside etc.

The mixture was separated by a centrifugal separator to obtain 800 ml of an aqueous extract. A 800 ml of n-butyl alcohol was added to the aqueous extract and the extraction was carried out for 30 minutes and the aqueous phase was separated after keeping it at a standstill. The extract was concentrated under a reduced pressure to obtain about 30 ml of syrup.

A 100 ml of methyl alcohol was added to the syrup to dissolve it under heating. The insoluble matter was separated and the filtrate was distilled under a reduced pressure to recover 50 ml of methyl alcohol. The residue was kept at cool room for one day. The precipitated crystals were filtered to obtain about 10 g of crude stevioside.

The crude crystals were dissolved in tetrahydrofuran to prepare 500 ml of the solution.

Chromatography apparatus HLC-802-UR manufactured by Toyo Soda Manufacturing Co., Ltd. was used and the styrene type gel having pore diameter of $2.5 \times 10^2$ Å (G 2000 H 8×2 manufactured by Toyo Soda Manufacturing Co., Ltd.) was packed as the column packing and tetrahydrofuran was fed at flow rate of 1.2 ml/min. to separate it at room temperature.

The peak for stevioside appeared about 20 min. of holding time. The stevioside in the stevia dried leaves was simply and quickly separated.

What is claimed is:

1. A method of resolving glycoside and non-glycoside sweet components having a molecular weight ranging from 250 to 1,000 in a natural sweet extract, which comprises:
    passing a solution of said natural sweet extract over a column of a porous organic gel having a pore diameter sufficient to achieve the desired resolution which is less than $1 \times 10^4$ Å and eluting the resolved glycoside and non-glycoside components from said gel with an eluant.
2. The method of claim 1, wherein said glycoside is stevioside, glycyrrhizin acid, or neohesperidin dihydrochalcone and said non-glycoside component is phyllodulcin or perillartine.
3. The method of claim 1, wherein said porous organic gel is a cross-linked styrene gel having a pore diameter of less than $1 \times 10^4$ Å and said eluent is a nonpolar organic solvent.
4. The method of claim 1, wherein said porous organic gel is a cross-linked starch gel having a pore diameter of less than $1 \times 10^4$ Å and said eluent is a mixture of water and a water miscible organic solvent.
5. The method of claim 1, wherein the pore diameter of said porous organic gel is less than $2.5 \times 10^2$ Å.
6. The method of claim 4, wherein said water miscible organic solvent is a $C_1$-$C_4$ alcohol, acetonitrile, dioxane, tetrahydrofuran, dimethylformamide or mixture thereof.
7. The method of claim 4, wherein said water-organic solvent mixture contains from 4 to 40 weight percent water.

* * * * *